US012629431B2

(12) United States Patent
Han et al.

(10) Patent No.: US 12,629,431 B2
(45) Date of Patent: May 19, 2026

(54) NANOPARTICLES WITH TUNABLE AFTERGLOW AND COMPOSITIONS AND METHODS THEREOF

(71) Applicant: University of Massachusetts, Boston, MA (US)

(72) Inventors: Gang Han, Shrewsbury, MA (US); Zhanjun Li, Worcester, MA (US)

(73) Assignee: University of Massachusetts, Westborough, MA (US)

( * ) Notice: Subject to any disclaimer, the term of this patent is extended or adjusted under 35 U.S.C. 154(b) by 636 days.

(21) Appl. No.: 17/467,412

(22) Filed: Sep. 6, 2021

(65) Prior Publication Data

US 2022/0096661 A1 Mar. 31, 2022

Related U.S. Application Data

(60) Provisional application No. 63/085,320, filed on Sep. 30, 2020.

(51) Int. Cl.
| | |
|---|---|
| *A61K 49/00* | (2006.01) |
| *A61K 9/51* | (2006.01) |
| *C09D 11/106* | (2014.01) |
| *C09D 11/50* | (2014.01) |
| *C09K 11/77* | (2006.01) |
| *G01N 21/64* | (2006.01) |

(52) U.S. Cl.
CPC ............ *A61K 49/0019* (2013.01); *A61K 9/51* (2013.01); *C09D 11/106* (2013.01); *C09D 11/50* (2013.01); *C09K 11/77492* (2021.01); *G01N 21/6456* (2013.01)

(58) Field of Classification Search
None
See application file for complete search history.

(56) References Cited

U.S. PATENT DOCUMENTS

| | | | |
|---|---|---|---|
| 2009/0155173 A1* | 6/2009 | Scherman | A61K 49/0067 424/9.1 |
| 2010/0295287 A1* | 11/2010 | Reichert | C09C 3/12 252/301.36 |
| 2018/0244992 A1* | 8/2018 | Han | A61Q 5/065 |

OTHER PUBLICATIONS

Li (A facile and effective method to prepare long-persistent phosphorescent nanospheres and its potential application for in vivo imaging, Oct. 4, 2012, Journal of Materials Chemistry, 22:24713) (Year: 2012).*
Van den Eeckhout (Persistent Luminescence in Non-Eu2+-Doped Compounds: A Review, Jul. 12, 2013, Materials: An Open Access Journal, 6:2789-2818) (Year: 2013).*
Barboza (Triclinic CdSiO3 structural, electronic, and optical properties from first principles calculations, Jul. 10, 2009, Journal of Physics D: Applied Physics, 42:155406) (Year: 2009).*
Jin-Yong (Trapping Effects in CdSiO3:In3+ Long Afterglow Phosphor, 2006, Chinese Physics Letter, 23(1):204-206) (Year: 2006).*
Manohara (Cadmium silicate nanopowders for radiation dosimetry application: Luminescence and dielectric studies, Journal or Asian Ceramic Societes, 2015, 3:188-197) (Year: 2015).*
Miranda (Synthesis and optical properties of BaTiO3: Eu3+@SiO2 glass ceramic nano particles, Sep. 16, 2014, Journal of Sol-Gel Science and Technology, vol. 72, 435-442) (Year: 2014).*
Rodrigues (Defect to R3+ energy transfer: colour tuning of persistent luminescence in CdSiO3, Nov. 25, 2013, Journal of Materials Chemistry C, 2:1612-1618) (Year: 2013).*

* cited by examiner

Primary Examiner — Michael G. Hartley
Assistant Examiner — Kaila A Craig
(74) Attorney, Agent, or Firm — Milstein Zhang & Wu LLC

(57) ABSTRACT

The invention provides novel nanoparticles with tunable and multi-color afterglow emission for extended time after excitation, and compositions thereof as well as methods for their preparation and use in various applications.

6 Claims, 11 Drawing Sheets

NANOPARTICLES WITH TUNABLE AFTERGLOW AND COMPOSITIONS AND METHODS THEREOF

PRIORITY CLAIMS AND RELATED APPLICATIONS

This application claims the benefit of priority to U.S. Provisional Application No. 63/085,320, filed Sep. 30, 2020, the entire content of which is incorporated herein by reference for all purposes.

TECHNICAL FIELDS OF THE INVENTION

The invention generally relates to nanoparticles and their use in imaging. More particularly, the invention provides novel nanoparticles with tunable and multi-color afterglow emission for extended time after excitation, and compositions thereof as well as methods for their preparation and use in various applications.

BACKGROUND OF THE INVENTION

High-contrast multiplex luminescence has received extensive attention in regard to in vitro and in vivo visualization through providing multi-color observation with high sensitivity and high spatial-temporal resolution. In order to achieve multiplex imaging, various kinds of fluorescence probes have been developed, such as organic dyes, proteins, and inorganic quantum dots. Yet, due to their extremely short lifetimes, the emissions of these fluorescence probes have to be simultaneously recorded with light excitation. Thus, the imaging quality of these probes is often heavily affected and compromised by severe scattering from the excitation light in addition to strong background autofluorescence from the samples. (Boens, et al. 2015 *Natl Acad Sci USA* 112, 3002; Jiang, et al. 2015 *Angew Chem Int Edit* 54, 5360; Kowada, et al. 2015 *Chem Sci* 6, 301; Shcherbakova, et al. 2018 *Nat Photonics* 12, 505.)

To mitigate this issue, efforts have been made to design molecules and nanoparticles with distinctive prolonged lifetimes. For example, instead of obtaining the true emission multi-colors, the lifetimes in these systems can be split to encode or be represented as different "colors". However, the lifetimes of these reported "multicolor" systems are within the range of micro- to a few milliseconds. Thus, currently, rather complicated time-gated devices and algorithms must be used to separate these lifetimes both from each other as well as from the inherent background signals, and the interference arising from the excitation light. (Li, et al. 2011 *Angew Chem Int Edit* 50, 6306; Gu, et al. 2018 *Acs Nano* 12, 4362; Rao, et al. 2010 *J Fluoresc* 20, 321; Chuang, et al. 2017 *Acs Nano* 11, 8185; Jiang, et al. 2015 *Angew Chem Int Edit* 54, 5360; Ma, et al. 2009 *Adv Mater* 21, 4768.)

Thus, there is an ongoing need for nanoparticles with true multicolor emissions and and improved lifetime and emission intensity.

SUMMARY OF THE INVENTION

The invention provides novel multicolor afterglow nanoparticles (AGNPs) possessing inherent long lifetime. The AGNPs of the invention are characterized by tailorable emission colors (e.g., blue, yellow, green, and white), substantially uniform particle size, and ultra-long afterglow emission, suitable for high-contrast multiplex emission imaging applications. The AGNPs can be prepared via a straightforward template method and are highly bright with controllable sizes and narrow size distribution, enabling them to perform high contrast multi-channel afterglow imaging in vitro and in vivo without the use of any complicated time-gating algorithms or systems.

In one aspect, the invention generally relates to a nanoparticle comprising $CdSiO_3$ and $SiO_2$, wherein $CdSiO_3$ and $SiO_2$ together form a hybrid crystalline lattice matrix comprising $CdSiO_3$ and $SiO_2$ molecules.

In another aspect, the invention generally relates to a composition comprising one or more nanoparticles disclosed herein.

In yet another aspect, the invention generally relates to an ink comprising nanoparticles disclosed herein.

In yet another aspect, the invention generally relates to a diagnostic probe comprising a nanoparticle disclosed herein.

In yet another aspect, the invention generally relates to a method for synthesizing nanoparticles. The method comprises: providing an aqueous solution of $Cd(NO_3)_2$; providing mesoporous $SiO_2$ nanoparticles having nanochannels therein; infusing the aqueous solution of $Cd(NO_3)_2$ into the nanochannels of the mesoporous $SiO_2$ nanoparticles; and performing calcination at a temperature in the range of about 850° C. to about 950° C. to form nanoparticles having substantially uniform spherical morphology and narrow size distribution.

In yet another aspect, the invention generally relates to an imaging method. The method comprises: directing one or more UV light beams at one or more nanoparticles disclosed herein; and detecting or analyzing an afterglow emission of the nanoparticles.

In yet another aspect, the invention generally relates to a method for authenticating a material or product. The method comprises incorporating or embedding one or more nanoparticles disclosed herein as one or more markers in the authentic material or product.

In yet another aspect, the invention generally relates to a method for identifying a counterfeit. The method comprises: incorporating or embedding one or more nanoparticles disclosed herein in an authentic material or product as one or more markers; directing one or more UV light beams at a test material or product to be authenticated; and detecting an afterglow emission of the test material or product to determine authenticity of the test material or product.

DETAILED DESCRIPTION OF THE INVENTION

Figure 1:
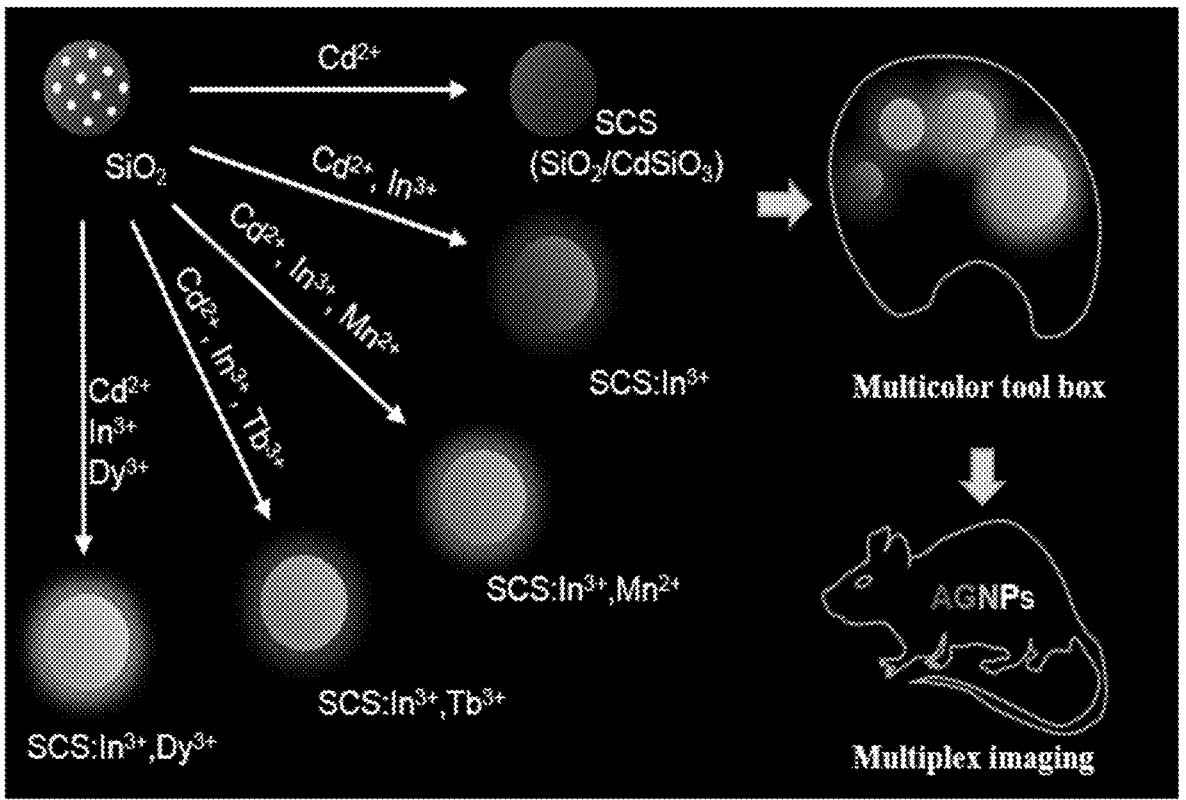
FIG. 1. A schematic illustration of the synthesis of multicolor AGNPs tool box for multiplex bio-imaging.

The invention is based in part on the discovery of novel nanoparticles with tunable and multi-color afterglow emission for extended time after excitation, and compositions thereof as well as methods for their preparation and use in various applications. In particular, uniform multicolor afterglow nanoparticles were successfully synthesized. For example, In$^{3+}$ was used to serve as an efficient sensitizer for blue SCS:In AGNPs. In$^{3+}$ co-doping affords a class of multicolor AGNPs with enhanced afterglow properties including SCS:In (blue), SCS: In, Mn (orange), SCS: In,Tb (green), SCS:In,Dy (white). The bottom-up template synthesis strategy disclosed herein let to AGNPs with high qualities such as uniform spherical morphology, narrow size distribution, and controllable sizes.

In contrast to fluorescence probes and the recent lifetime encoded "multicolor" systems, the AGNPs disclosed herein are unique with an inherently superior lifetime, maintain afterglow period of time (e.g., for seconds to hours, or even days) after the cessation of the excitation. The long or ultra-long lifetime of afterglow afford enough time to turn off the excitation, wait for all the optical background signals to decay completely, and then perform afterglow imaging by manual or automated manipulation. The multicolor AGNPs can perform high contrast multi-channel afterglow imaging in vitro and in vivo without the use of any complicated time-gating algorithms or systems, which existing tools are unable to do.

Thus, the intrinsically unique ultra-long life time of AGNPs disclosed herein provide a new and true color multiplexing solution with superior signal-to-background contrast imaging capability, while completely avoiding the need for any time-gated device and algorithm.

Multiplex afterglow imaging can be performed by using multicolor AGNPs disclosed herein. Benefited by the abundant luminescence spectra, excellent geometrical characteristic, and unique high-contrast afterglow imaging ability, the AGNPs disclosed are useful in wide-ranging applications that require diverse color options, such as optical anti-counterfeit technology, ultra-sensitive optical pre-clinical animal bio-imaging, time-resolved luminescence analysis and multi-color diagnosis.

In one aspect, the invention generally relates to a nanoparticle comprising CdSiO$_3$ and SiO$_2$, wherein CdSiO$_3$ and SiO$_2$ together form a hybrid crystalline lattice matrix comprising CdSiO$_3$ and SiO$_2$ molecules.

In certain embodiments of the nanoparticle, the molar ratio of CdSiO$_3$ to SiO$_2$ is in the range from about 1% to about 50% (e.g., from about 1% to about 40%, from about 1% to about 30%, from about 1% to about 20%, from about 1% to about 10%, from about 1% to about 5%, from about 2% to about 50%, from about 5% to about 50%, from about 10% to about 50%, from about 2% to about 15%, from about 2% to about 10%, from about 5% to about 10%).

In certain embodiments, the molar ratio of CdSiO$_3$ to SiO$_2$ is in the range from about 1% to about 10%.

In certain embodiments, the nanoparticle further comprises a first dopant. The first dopant may be selected from the group consisting of In$^{3+}$, Y$^{3+}$, Lu$^{3+}$, Gd$^{3+}$ and Eu$^{3+}$. In certain embodiments, the first dopant is In$^{3+}$.

In certain embodiments, the molar ratio of the first dopant to CdSiO$_3$ is in the range from about 0.1% to about 10% (e.g., from about 0.1% to about 7%, from about 0.1% to about 5%, from about 0.1% to about 2%, from about 0.1% to about 1%, from about 0.5% to about 10%, from about 1% to about 10%, from about 5% to about 10%, from about 0.5% to about 2%, from about 2% to about 6%).

In certain embodiments, the nanoparticle further comprises a second dopant selected from the group consisting of Mn$^{2+}$, Tb$^{3+}$, Dy$^{3+}$ and Cr$^{3+}$. In certain embodiments, the second dopant is Mn$^2$. In certain embodiments, the second dopant is Tb$^{3+}$. In certain embodiments, the second dopant is Dy$^{3+}$. In certain embodiments, the second dopant is Cr$^{3+}$.

In certain embodiments, the molar ratio of the first dopant to the second dopant is in the range from about 0.1 to about 10 (e.g., from about 0.1 to about 0.3, from about 0.3 to about 0.5, from about 0.5 to about 0.8, from about 0.8 to about 1, from about 1 to about 3, from about 3 to about 5, from about 5 to about 8, from about 8 to about 10, from about 0.5 to about 5, from about 0.2 to about 2).

In certain embodiments, the nanoparticle comprises In$^{3+}$ as the first dopant and Mn$^{2+}$ as the second dopant. In certain embodiments, the nanoparticle comprises In$^{3+}$ as the first dopant and Tb$^{3+}$ as the second dopant. In certain embodiments, the nanoparticle comprises In$^{3+}$ as the first dopant and Dy$^{3+}$ as the second dopant. In certain embodiments, the nanoparticle comprises In$^{3+}$ as the first dopant and Cr$^{3+}$ as the second dopant.

In certain embodiments, the nanoparticle further comprises a third dopant.

In certain embodiments, the nanoparticle has a size in the range of about 20 nm to about 2,000 nm (e.g., about 20 nm to about 2,000 nm, about 20 nm to about 1,000 nm, about 20 nm to about 500 nm, about 20 nm to about 200 nm, about 20 nm to about 100 nm, about 100 nm to about 2,000 nm, about 200 nm to about 2,000 nm, about 500 nm to about 2,000 nm, about 50 nm to about 200 nm, about 50 nm to about 100 nm, about 100 nm to about 500 nm). In certain embodiments, the nanoparticle has a size in the range of about 20 nm to about 200 nm. In certain embodiments, the nanoparticle has a size in the range of about 50 nm to about 100 nm.

In certain embodiments, the nanoparticle is characterized by an afterglow that is tunable from blue to orange, e.g., by adjusting the molar ratio of the first dopant to $CdSiO_3$ and/or the molar ratio of the first dopant to the second dopant.

In certain embodiments, the nanoparticle is characterized by an afterglow lasting 1 hour or longer after UV excitation. In certain embodiments, the nanoparticle is characterized by an afterglow lasting about 1 to about 6 hours or longer after UV excitation. In certain embodiments, the nanoparticle is characterized by an afterglow lasting about 6 to about 24 hours after UV excitation.

It is noted that the term "nanoparticle" as used herein may refer to a single particle or a plurality of a type of nanoparticle. By way of example, a nanoparticle that comprises $In^{3+}$ as the first dopant and $Mn^{2+}$ as the second dopant refers to a single particle or a plurality of such type of nanoparticle. The term "nanoparticles" as used herein refers to a plurality of a type of nanoparticle or mixed types of nanoparticles.

In another aspect, the invention generally relates to a composition comprising one or more nanoparticles disclosed herein.

In certain embodiments, the composition comprises nanoparticles having co-dopants $In^{3+}$ and $Mn^{2+}$. In certain embodiments, the composition comprises nanoparticles having co-dopants $In^{3+}$ and $Tb^{3+}$. In certain embodiments, the composition comprises nanoparticles having co-dopants $In^{3+}$ and $Dy^{3+}$. In certain embodiments, the composition comprises nanoparticles having co-dopants $In^{3+}$ and $Cr^{3+}$.

In certain embodiments of the composition, the sizes of the nanoparticles are substantially uniform.

In certain embodiments of the composition, the sizes of the nanoparticles are within the range from about 20 nm to about 2,000 nm (e.g., about 20 nm to about 2,000 nm, about 20 nm to about 1,000 nm, about 20 nm to about 500 nm, about 20 nm to about 200 nm, about 20 nm to about 100 nm, about 100 nm to about 2,000 nm, about 200 nm to about 2,000 nm, about 500 nm to about 2,000 nm, about 50 nm to about 200 nm, about 50 nm to about 100 nm, about 100 nm to about 500 nm). In certain embodiments, the sizes of the nanoparticles are within the range from about 20 nm to about 200 nm. In certain embodiments, the sizes of the nanoparticles are within the range from about 20 nm to about 100 nm.

In certain embodiments, the composition is an aqueous solution.

In certain embodiments, the composition comprises a water-soluble polymer. In certain embodiments, the water-soluble polymer is polyvinylpyrrolidone. In certain embodiments, the water-soluble polymer (e.g., polyvinylpyrrolidone) is present in about 1% to about 10% by weight.

In yet another aspect, the invention generally relates to an ink comprising nanoparticles disclosed herein.

In yet another aspect, the invention generally relates to a diagnostic probe comprising a nanoparticle disclosed herein.

In yet another aspect, the invention generally relates to a method for synthesizing nanoparticles. The method comprises: providing an aqueous solution of $Cd(NO_3)_2$; providing mesoporous $SiO_2$ nanoparticles having nanochannels therein; infusing the aqueous solution of $Cd(NO_3)_2$ into the nanochannels of the mesoporous $SiO_2$ nanoparticles; and performing calcination at a temperature in the range of about 850° C. to about 950° C. to form nanoparticles having substantially uniform spherical morphology and narrow size distribution.

In certain embodiments, the aqueous solution of $Cd(NO_3)_2$ further comprises a precursor to the first dopant.

In certain embodiments, the aqueous solution of $Cd(NO_3)_2$ further comprises a precursor to the second dopant.

In certain embodiments, the resulting nanoparticles are in the range of about 20 nm to about 2,000 nm (e.g., about 20 nm to about 2,000 nm, about 20 nm to about 1,000 nm, about 20 nm to about 500 nm, about 20 nm to about 200 nm, about 20 nm to about 100 nm, about 100 nm to about 2,000 nm, about 200 nm to about 2,000 nm, about 500 nm to about 2,000 nm, about 50 nm to about 200 nm, about 50 nm to about 100 nm, about 100 nm to about 500 nm).

In certain embodiments, the resulting nanoparticles are characterized by a narrow size distribution. In certain embodiments, the relative variance of nanoparticle size is less than 30% measured by transmission electron microscope, which is controlled by the mesoporous silica nanotemplate. In certain embodiments, the relative variance of nanoparticle size is less than 20%. In certain embodiments, the relative variance of nanoparticle size is less than 15%. In certain embodiments, the relative variance of nanoparticle size is less than 10%. In certain embodiments, the relative variance of nanoparticle size is less than 5%.

In yet another aspect, the invention generally relates to an imaging method. The method comprises: directing one or more UV light beams at one or more nanoparticles disclosed herein; and detecting or analyzing an afterglow emission of the nanoparticles.

In certain embodiments, the one or more nanoparticles are mixed with or in an in vitro biological test sample.

In certain embodiments, the one or more nanoparticles are mixed with or in an in vivo biological test sample.

In yet another aspect, the invention generally relates to a method for authenticating a material or product. The method comprises incorporating or embedding one or more nanoparticles disclosed herein as one or more markers in the authentic material or product.

In yet another aspect, the invention generally relates to a method for identifying a counterfeit. The method comprises: incorporating or embedding one or more nanoparticles disclosed herein in an authentic material or product as one or more markers; directing one or more UV light beams at a test material or product to be authenticated; and detecting an afterglow emission of the test material or product to determine authenticity of the test material or product.

In certain embodiments, one or more UV light beams comprising a wavelength in the range of about 180 nm to about 350 nm.

In certain embodiments, the afterglow emission comprises two or more colors. In certain embodiments, the afterglow emission comprises three or more colors. In certain embodiments, the afterglow emission comprises four or more colors.

In certain embodiments, the afterglow emission comprises one or more colors selected from blue, yellow, green and white. In certain embodiments, the afterglow emission comprises two or more colors selected from blue, yellow, green and white.

The following examples are meant to be illustrative of the practice of the invention and not limiting in any way.

Examples

While multicolor bulk afterglow materials are known, few reports can be found on their colloidal nanoscale counterparts, especially AGNPs with the same luminescent matrix which possess tunable color and intense afterglow emission. The main reason is that simple solid state synthesis needs high temperature annealing process that leads to bulk granular sizes, which makes AGNPs difficult to obtain. Further, simply decreasing the particle sizes of afterglow materials usually leads to dramatically attenuated afterglow intensity which hinders their latent advanced applications. Thus, AGNPs with uniform small sizes and intense tunable afterglow emissions are urgently being pursued and not yet realized before this publication.

As disclosed herein, multicolor AGNPs with a uniform morphology were prepared via a straightforward bottom-up template synthesis method. The resultant AGNPs exhibited uniform size and were systematically tailorable and had highly bright afterglow emissions (blue, yellow, green, and white) (FIG. 1).

We set off on our multicolor AGNP synthesis using mesoporous $SiO_2$ nanoparticles as the templates to in situ grow diverse ion doped $SiO_2/CdSiO_3$ (SCS) hybrid AGNPs. The pristine $CdSiO_3$ is known as a reasonable optical matrix for the study of the afterglow in bulk crystals. The rare earth ions (e.g., Y, Lu, or Gd) doped bulk $CdSiO_3$ crystals were reported to be able to adjust to afterglow wavelength but their afterglow intensities were found to be rather weak and to only last for only several minutes. (Liu, et al. 2014 *J Mater Chem C* 2, 1612.)

Figure 6:
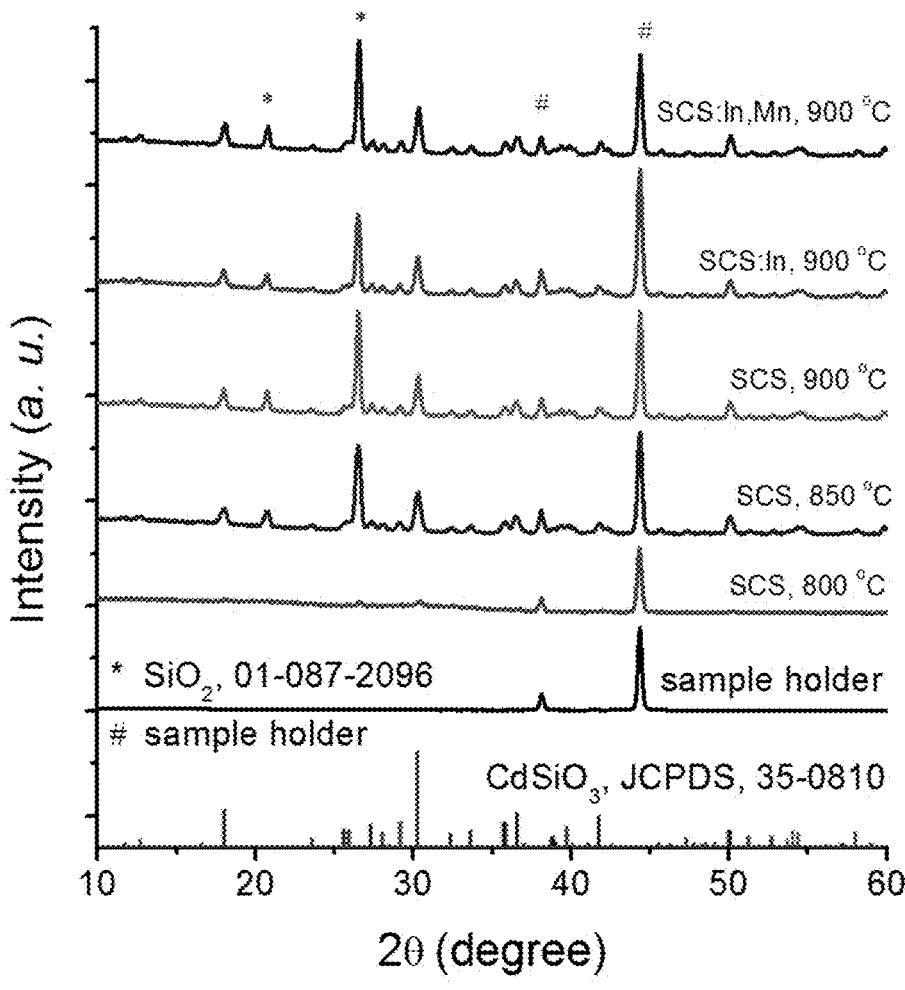
FIG. 6. X-ray diffraction patterns of SCS, SCS:In$_{0.02}$, and SCS:In$_{0.02}$,Mn$_{0.001}$ synthesized at different temperatures.

Here, to construct the hybrid SCS matrix, $Cd(NO_3)_2$ aqueous solution was first infused into the nanochannels of mesoporous $SiO_2$ nanoparticles to in situ grow monoclinic $CdSiO_3$ via subsequent calcination reaction at 900° C. Since such a monoclinic $CdSiO_3$ lattice has a crystal structure of one-dimensional chains of edge-sharing $SiO_4$ tetrahedrons, it was observed to be simultaneously interconnected with $SiO_2$ to form a hybrid SCS lattice. The hybrid SCS lattice matrix was confirmed by the XRD patterns (FIG. 6). It is worth noting that in this reaction we chose 900° C. as the optimal synthetic condition, as it is critical that the reaction temperatures are higher than 850° C. in order to generate a monoclinic phase $CdSiO_3$. However, like the literature reports, a higher temperature above 950° C. was found lead to unfavorable $SiO_2$ particle deformation and aggregation. (Zhan-Jun, et al. 2012 *J Mater Chem* 22, 24713.)

Figure 2:
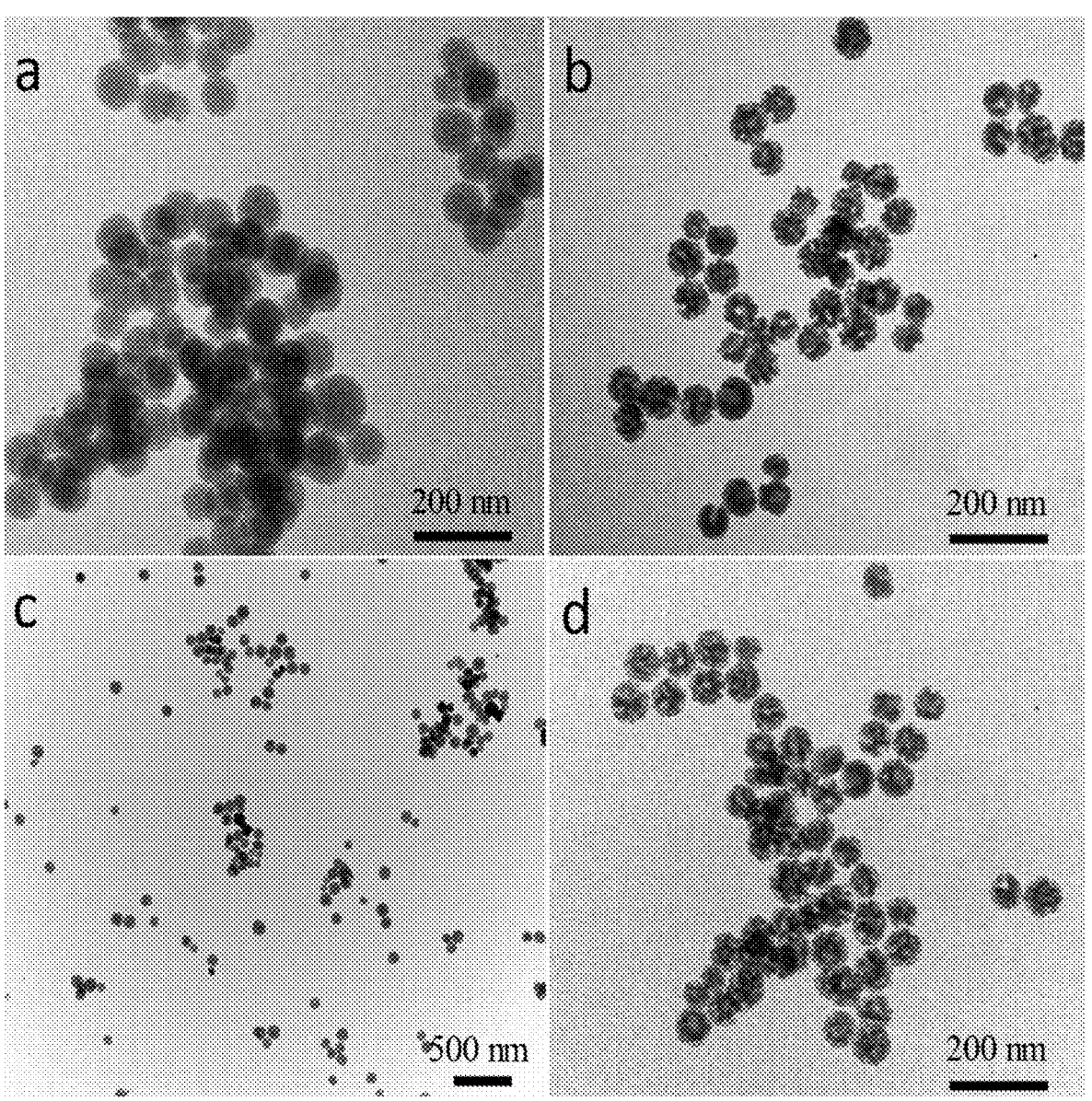
FIG. 2. TEM images of (a) original mesoporous $SiO_2$ template, (b) SCS and (c, d) SCS:In calcinated at 900° C.

The as-synthesized SCS nanoparticles possessed uniform spherical morphology (ca. 70 nm) with narrow size distribution (FIG. 2). Given that all of the silica and $Cd^{2+}$ precursor were converted into the SCS, the molar ratio of $CdSiO_3$ vs $SiO_2$ in SCS is calculated to be 6.39%.

Figure 3:
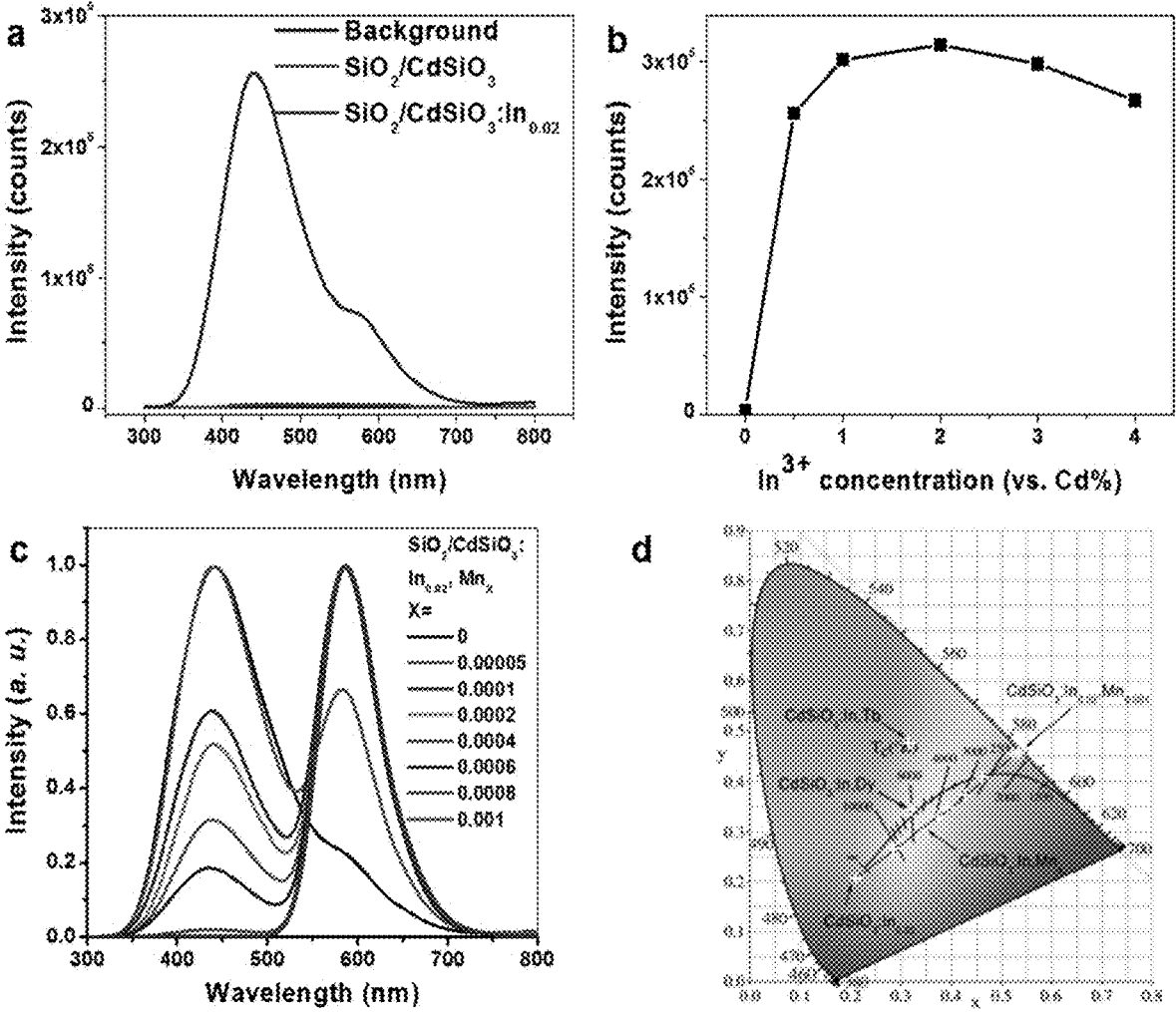
FIG. 3. Afterglow properties of SCS:In and SCS:In,Mn. (a) Afterglow spectra of SCS:In vs. SCS, (b) influence of $In^{3+}$ doping concentration on the afterglow intensity at 20 s after the cessation of the UV excitation (254 nm, 5 min), (c) normalized afterglow spectra of $SCS:In_{0.02},Mn_x$, x varies from 0.00005 to 0.001 (vs. Cd), (d) CIE (Commission Internationale de L'Eclairage) chromaticity diagram of the multicolor AGNPs.

Next, the afterglow property of the SCS nanoparticles was investigated. Interestingly, we found that unlike the reported pure bulk $CdSiO_3$ with blue afterglow, the SCS nanoparticles actually exhibited insignificant afterglow luminescence after cessation of 254 nm light excitation (FIG. 3a). (Liu, et al. 2014 *J Mater Chem C* 2, 1612.) This finding is likely due to the difference in internal energy traps between conventional pure $CdSiO_3$ and the hybrid lattice of SCS.

Figure 7:
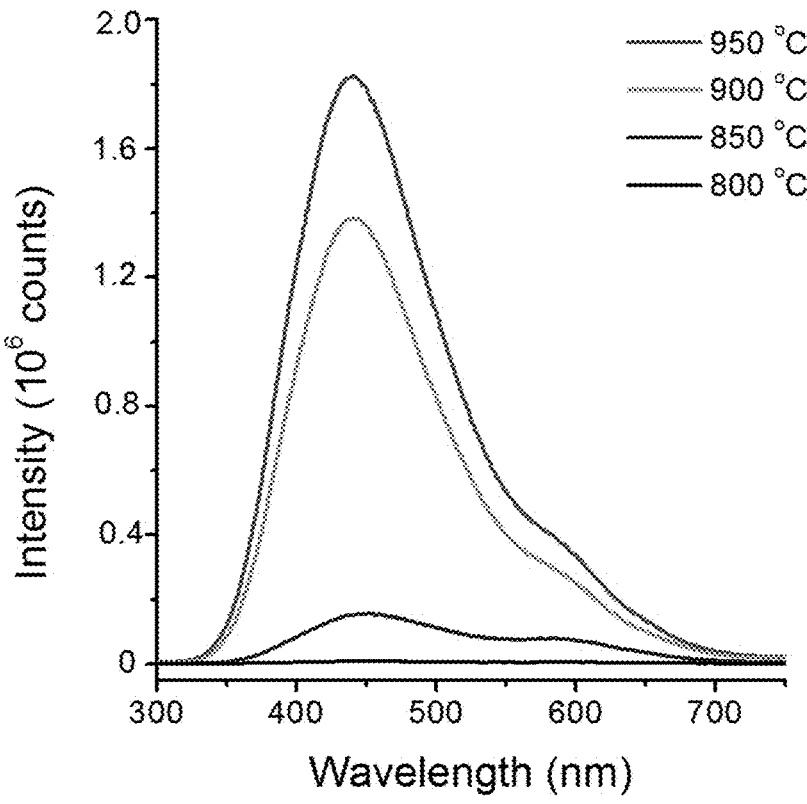
FIG. 7. Afterglow spectra of SCS:In$_{0.02}$ synthesized at various annealing temperatures 20 s after the cessation of the UV excitation (5 min 254 nm illumination).
Figure 8:
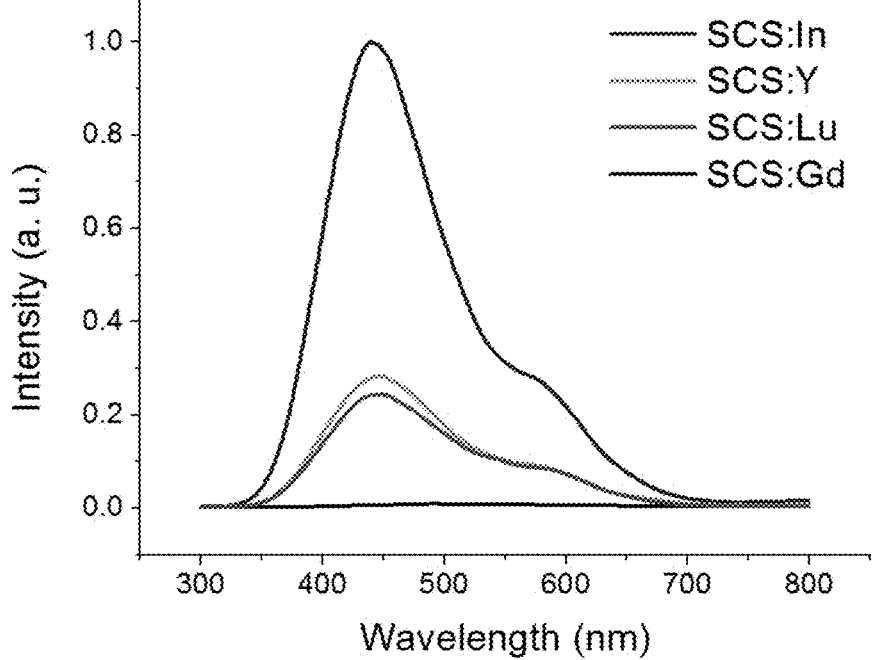
FIG. 8. Afterglow spectra of SCS nanoparticles doped with 2% (vs Cd) of In$^{3+}$, Y$^{3+}$, Lu$^{3+}$, Gd$^{3+}$ acquired at 20 s after the cessation of the UV excitation (254 nm for 5 min).

In order to activate the afterglow luminescence of SCS nanoparticles, we then went on to examine a series of different trivalent ions (i.e., $In^{3+}$ and rare earth $Y^{3+}$, $Lu^{3+}$, or $Gd^{3+}$) as possible afterglow activators by infusing the precursor solution containing the respective trivalent ions and the $Cd^{3+}$ ions into mesoporous $SiO_2$ nanosphere template followed by calcination reaction at 900° C. Among them, we found that $In^{3+}$ ion stood out and is the best ion candidate with respect to most effectively lighting up the latent blue afterglow luminescence within the pure SCS nanoparticles (FIGS. 7 and 8). In addition, our study shows that the SCS host is sensitive to the $In^{3+}$ dopant and we found that even small amounts (0.5% vs. Cd) doping of $In^{3+}$ can turn on the latent afterglow in SCS nanoparticles and that the optimal concentration of $In^{3+}$ dopant was observed to be 2% vs. Cd (FIG. 3b).

Since $In^{3+}$ itself has no intermediate electronic energy levels within the bandgap of $CdSiO_3$ (5.4 eV), we attributed the blue afterglow emission of the SCS:In AGNPs to additional energy traps resulting from the substitution of $In^{3+}$ with $Cd^{2+}$ as well as the consequent localized electron-hole recombination process between intrinsic defects (Cd or O vacancy). We further explored the possibility to extend the afterglow emissions of pure SCS AGNPs by using co-dopant of $In^{3+}$ and $Mn^{2+}$ ions. With the increase of the $Mn^{2+}$ doping concentration from 0.00005:1 to 0.001:1 (Mn vs. Cd), we observed that the original afterglow peak at 438 nm and a relatively weak shoulder peak at 580 nm from the intrinsic oxygen vacancy defects of $CdSiO_3$ decreased gradually (FIG. 3c). Meanwhile, the SCS:In, Mn nanoparticles show a new afterglow peak at 580 nm, corresponding to characteristic $^4T_{1g}(G)$ to $^6A_{1g}(S)$ transition of $Mn^{2+}$. This significant afterglow color shifting indicates that the energy transfer occurred from the intrinsic defect of $CdSiO_3$ to $Mn^{2+}$ ions in SCS:In,Mn. Thus, by increasing the doping concentration of $Mn^{2+}$ in SCS:In, the afterglow emission colors of SCS:In, Mn nanoparticles can be systematically tailored from blue to orange, as shown in the CIE (Commission Internationale de L'Eclairage) chromaticity diagram in FIG. 3d.

Figure 4:
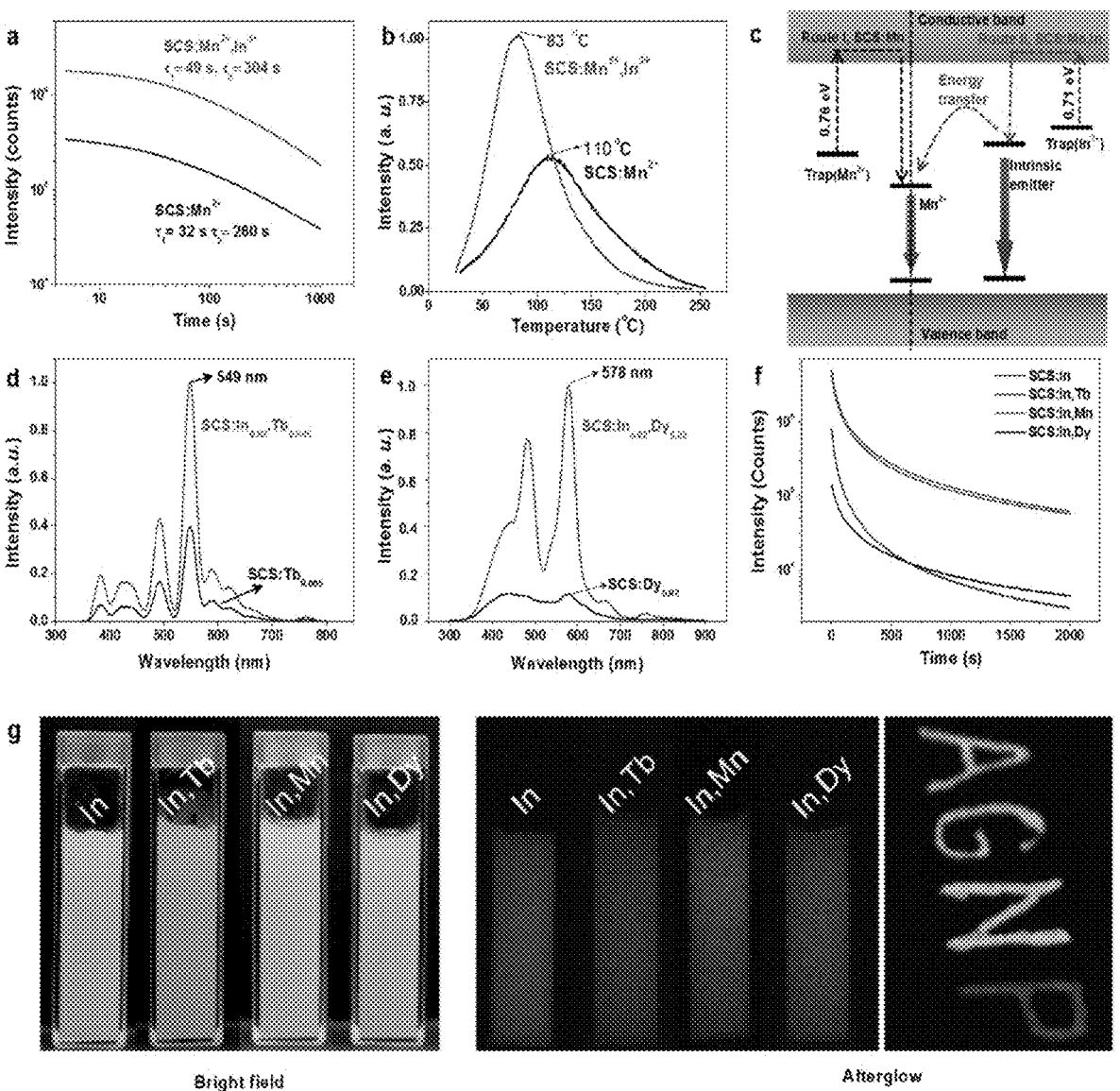
FIG. 4. Mechanism of enhanced afterglow in $In^{3+}$-codoped SCS AGNPs and their multiplex true color anticounterfeiting application. (a) afterglow decay curves of $SCS:Mn_{0.001},In_{0.02}$ and $SCS:Mn_{0.001}$, (b) thermal stimulated luminescence (TSL) of $SCS:In_{0.02},Mn_{0.001}$ and $SCS:Mn_{0.001}$, (c) proposed afterglow mechanism, (d) $SCS:Tb_{0.005}$ and $SCS:In_{0.02},Tb_{0.005}$, (e) $SCS:Dy_{0.02}$ and $SCS:In_{0.02},Dy_{0.02}$, (f) afterglow emission decay curves monitored from 10 s after the stop of the UV excitation (254 nm, 5 min), (g) true color optical images of AGNP colloidal dispersion in water taken by a commercial digital camera, left: bright field, middle: afterglow of colloidal dispersion, right: afterglow of handwriting. The afterglow spectra were acquired at 20 s after the cessation of the UV excitation (254 nm, 5 min).

To further study the afterglow mechanism of SCS:In,Mn, the afterglow decay of SCS:In,Mn and stringent control $Mn^{2+}$ doped SCS (SCS:Mn) nanoparticles were compared. As shown in FIG. 4a, both the decay curves can be fitted with a dual-exponential eq. (1):

$$Y=A_1*\exp(-x/\tau_1)+A_2*\exp(-x/\tau_2)+A_0 \qquad (1)$$

$\tau_1$, $\tau_2$ are decay lifetimes that represent the fast and slow decay periods in typical afterglow materials, respectively. $A_0$, $A_1$, and $A_2$ are the constants in the equation. As a result, SCS:In,Mn showed prolonged afterglow lifetimes of 49 s and 304 s for $\tau 1$ and $\tau 2$, respectively, as compared to 32 s and 260 s for SCS:Mn (FIG. 4a). Moreover, compared to SCS:In,Mn, SCS:Mn nanoparticles exhibit notably weaker afterglow emission. The distinct afterglow decay lifetime and intensity differences in SCS:In,Mn and SCS:Mn nanoparticles are considered be related to the trap depths. So far, we have further conducted a study of thermal stimulated luminescence (TSL) spectra for SCS:Mn and SCS:In, Mn, as TSL is currently considered to be the most general tool used in the field to study trap depth and distribution in afterglow materials. The resultant energy levels of the trap depths were calculated according to eq. (2). (Wang, et al. 2019 *J Mater Chem C* 7, 8303; Du, et al. 2019 *Sci Rep-Uk* 9.)

9

$$E = T_m(K)/500(K) \qquad (2)$$

$T_m$ is the thermal stimulated luminescence (TSL) peak position.

We found that the introduction of co-dopant In³⁺ ions leads the trap depth to shift from 0.76 eV in SCS:Mn to a shallower level of 0.71 eV in SCS: In, Mn (FIG. 4b). Note that it is well-known that a trap depth of ca. 0.70 eV is optimal for room temperature afterglow emission. (Maldiney, et al. 2011 *J Am Chem Soc* 133, 11810.) Thus, compared to the original energy level of SCS:Mn, the decreased trap energy in SCS: In, Mn is attributed to enhanced afterglow emission at room temperature.

Based on the above analysis and results, we further proposed possible energy transfer mechanisms for this enhanced afterglow, as demonstrated in FIG. 4c. For the afterglow mechanism of SCS:Mn (Route I in FIG. 4c), due to the fact that SCS itself was found to have no afterglow, the excitation energy is considered to be stored in Mn-related energy traps (Trap (Mn²⁺)). At room temperature, the trapped energy can then be slowly released via thermal perturbation and subsequently returned to the ground state via the radiative relaxation of the emitter (Mn²⁺). In contrast, for the afterglow mechanism in SCS:In,Mn, (Route II in FIG. 4c), the doping of In³⁺ not only generates shallower and more favorable In-related traps (Trap(In³⁺)), it also increases the concentration of the energy traps by the substitution of Cd²⁺ with In³⁺. Since the number of the In³⁺-doping induced intrinsic emitters (oxygen vacancy) are abundant (2% vs Cd), energy transfer from these intrinsic emitters to Mn²⁺ can take place. Thus, enhanced afterglow can be generated from route II and colorful emission can be achieved by tuning the concentration of Mn²⁺ vs In³⁺.

Figure 9:
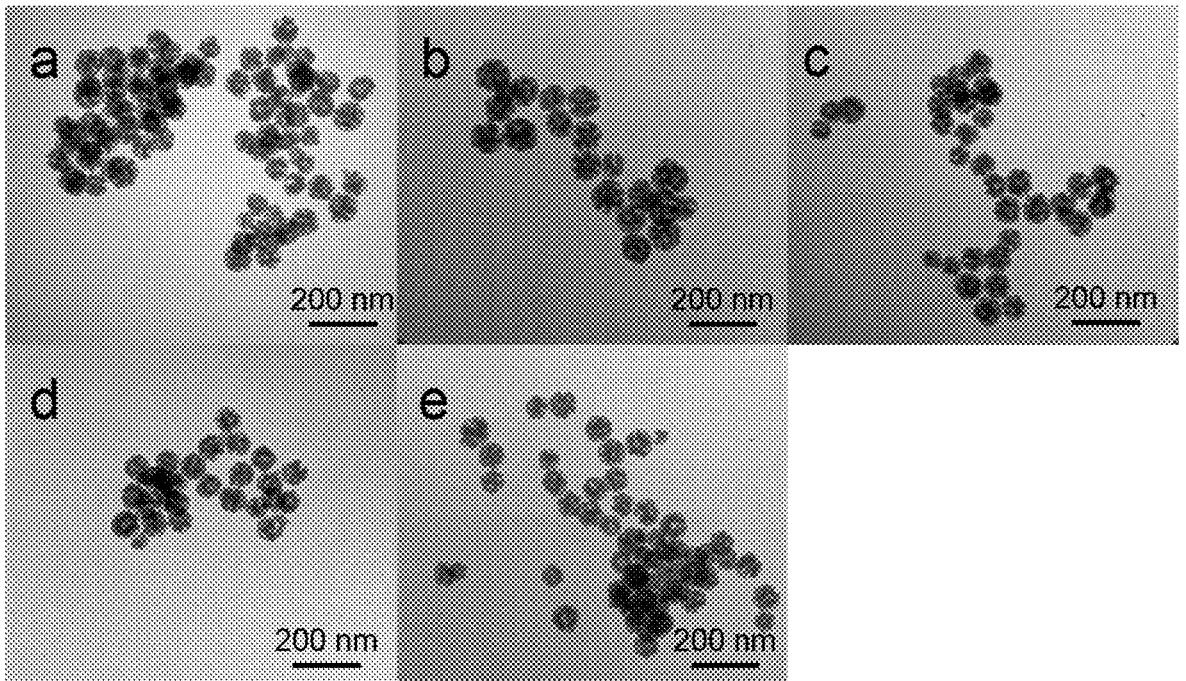
FIG. 9. TEM images of the as-synthesized (a) SCS:In,Mn, (b) SCS:Tb, (c) SCS:In,Tb, (d) SCS:Dy, (e) SCS:In,Dy.

Next, we envision that the In³⁺ ion mediated afterglow enhancement may be amenable to other SCS based AGNPs, so as to extend the wider options of afterglow emission colors. In order to test this hypothesis, we further synthesized In³⁺ co-doped SCS:In,Tb and SCS:In,Dy AGNPs, as well as stringently controlled SCS:Tb and SCS:Dy AGNPs (FIG. 9). When compared to their single ion doped counterparts (SCS:Tb and SCS:Dy), both of the co-doped nanoparticles (SCS:In,Tb and SCS:In,Dy) show stronger afterglow emissions (FIG. 4d, 4e). In the case of Tb-doped nanoparticles, the intensity of the characteristic afterglow peak at 549 nm of SCS:In,Tb is 2.5-fold stronger than that of SCS:Tb. Similarly, for Dy-doped nanoparticles, SCS:In, Dy exhibits much stronger afterglow emission than SCS:Dy, and the intensity of the afterglow peak at 578 nm increased by ca. 10 times. Furthermore, afterglow emission decay curves verified that the outstandingly long afterglow of these new AGNPs can be detected for >2000 s, and that the afterglow time of the co-doped nanoparticles have much longer afterglow lifetimes than that of their single ion doped counterparts (FIG. 4f). Note that afterglow time is defined by the detectable signals in the fluorometer after turning off the excitation light.

These multicolor AGNPs, including SCS:In, SCS:In,Mn, SCS:In,Tb, and SCS:In,Dy, can be readily dispersed in aqueous solution with polyvinylpyrrolidone (FIG. 4g). After the cessation of the UV excitation, these water soluble AGNPs dispersions retain bright emissions. Additionally, these water soluble AGNPs with different compositions can be directly used as the "color-ink" for true color anticounterfeiting afterglow imaging. As shown in FIG. 4g, distinct bright multicolor afterglow can be observed in the hand-written letters "A", "G", "N", "P". ("A" was written by SCS:In, "G" was written by SCS:In,Tb, "N" was written by SCS:In,Mn, and "P" was written by SCS:In,Dy). It is worth noting that, as these signals are sufficiently bright, true color afterglow signals can be clearly acquired by using a conventional Digital Single Lens Reflex camera. This indicates the potential of multicolored AGNPs as a practical straightforward tool for anticounterfeiting, as well as other information encryption applications.

Figure 5:
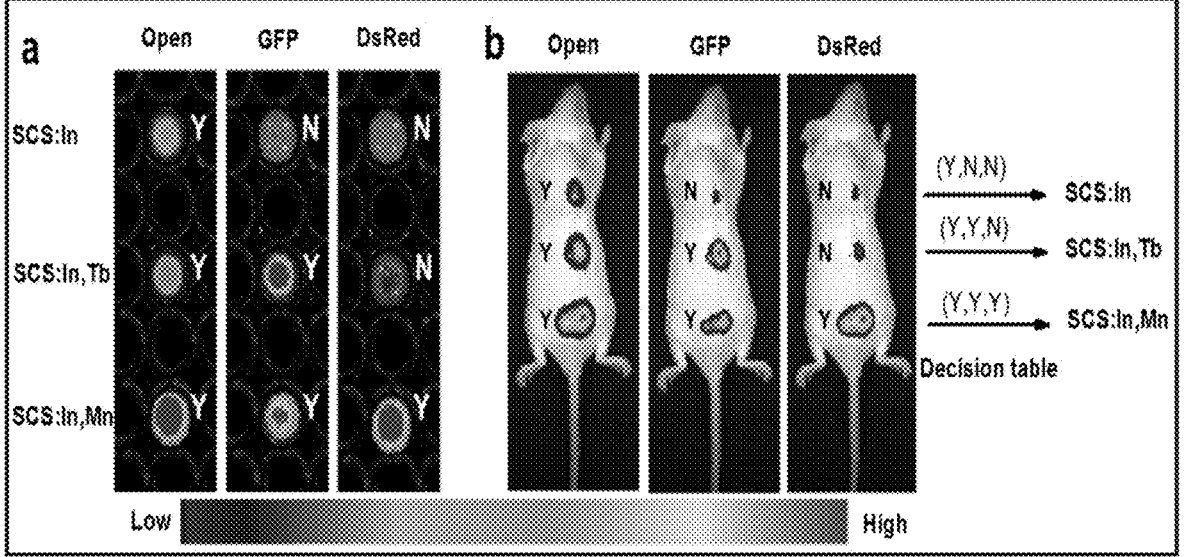
FIG. 5. Afterglow imaging of the multicolor AGNPs. (a) Imaging in vitro. Selective imaging coupled with diverse optical filters in 96-well plate by using IVIS animal imaging system coupled with a EMCCD camera (1 s exposure). The concentration of the AGNP colloidal dispersion is 5 mg/mL. The afterglow images were taken as soon as possible after the stop of UV irradiation (254 nm, 6 w, 5 min). (b) Imaging in vivo. Selective imaging coupled with diverse optical filters was performed in a subcutaneously injected mouse by using IVIS animal imaging system coupled with an EMCCD camera (1 s exposure). The concentration of the AGNP colloidal dispersion is 5 mg/mL. The dosage of the injection is 50 μL. The afterglow intensity is expressed in false color. Y: yes, N: no.

Biological luminescent preclinical animal imaging is considered one of the promising applications of AGNPs. (Maldiney, et al. 2011 *J Am Chem Soc* 133, 11810.) In addition to the true color anticounterfeiting afterglow imaging, we then explored the feasibility for time-gating free afterglow imaging using our water soluble multicolor AGNPs. As shown in FIG. 5, in our study, afterglow images can be readily taken with a suite of simple built-in filters in the conventional bioluminescence imaging system with a set of built-in filters in the same mouse. Vividly, signals from SCS:In, SCS:In,Tb, and SCS:In,Mn can be detected without any filters. When adding a GFP filter (515 nm-575 nm), both the afterglow from SCS:In,Tb and SCS:In,Mn can be observed while the signal of SCS:In becomes hardly detectable. Moreover, by choosing a DsRed filter (575 nm-650 nm), only the signal from SCS:In,Mn can be detected. Based on these results, a logic decision table can be generated for telling the difference of the colors by taking intense detectable signals as 'yes' (Y) and weak undetectable signals as 'no' (N), as shown in FIG. 5a and Table 1. In this case, we can differentiate the colors of the three samples based on the detected condition logic values (Y or N) and make the corresponding 'decisions' without the aids of time-gating systems.

TABLE 1

| Logic decision table for imaging identification of multi AGNPs. | | | |
|---|---|---|---|
| Conditions | | | Decisions |
| Open | GFP | DsRed | Species |
| Y | N | N | SCS: In |
| Y | Y | N | SCS: In, Tb |
| Y | Y | Y | SCS: In, Mn |

Y: yes, N: no.

Figure 10:
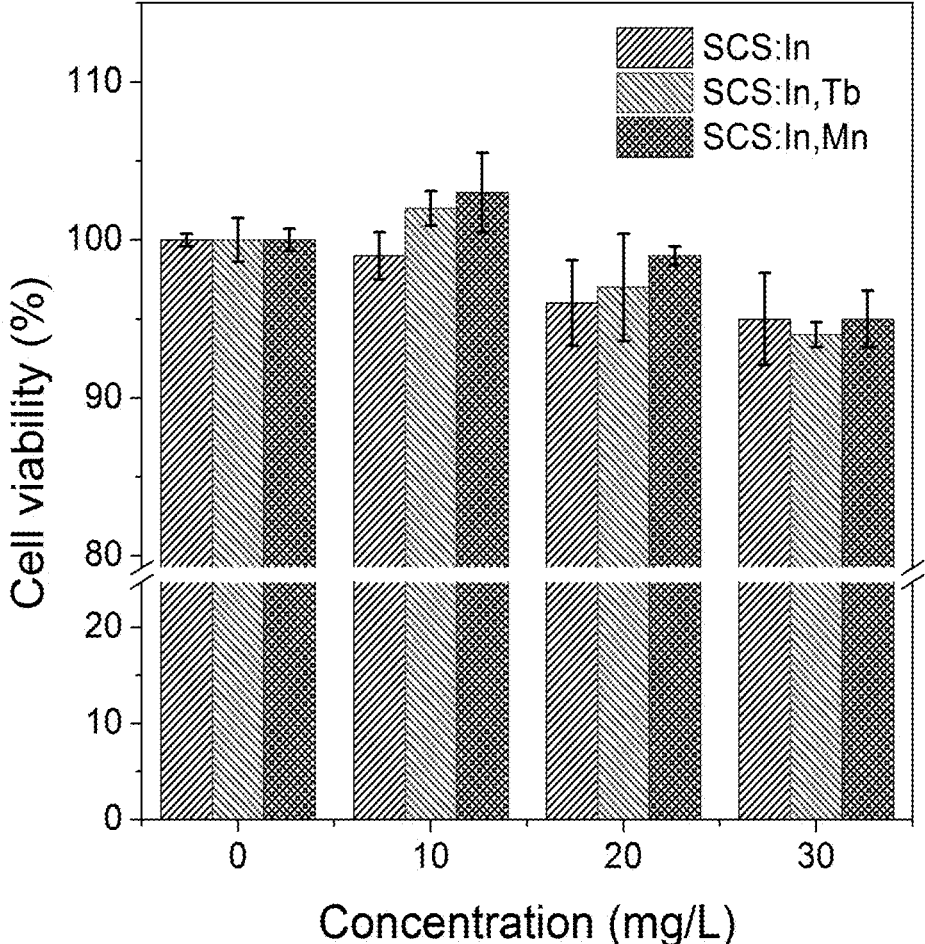
FIG. 10. Cytotoxicity of the multicolor AGNPs.
Figure 11:
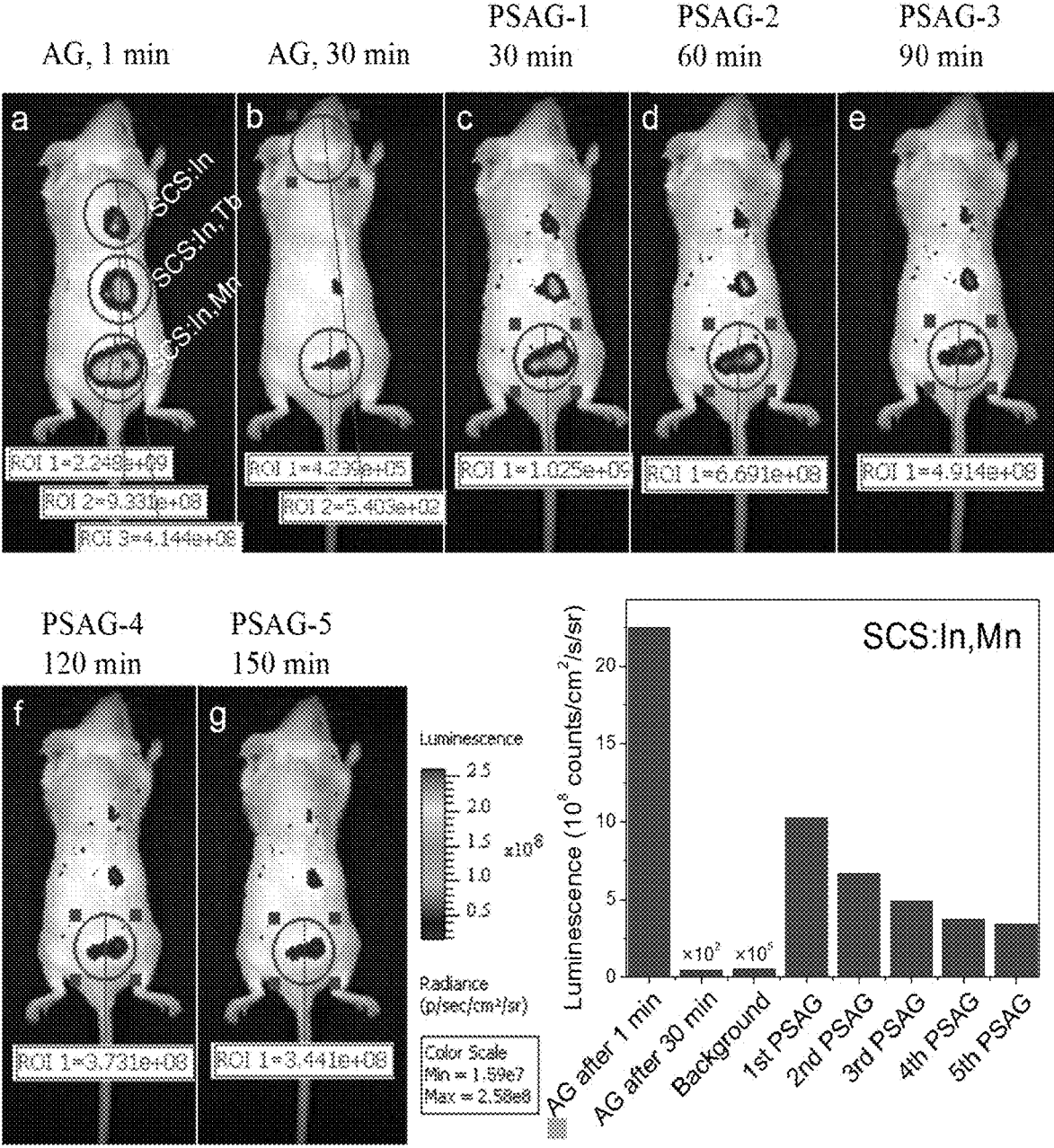
FIG. 11. Photostimulated afterglow imaging of subcutaneously injected mouse (1 s exposure). (a, b) Initial afterglow imaging after ex vivo UV excitation (254 nm), (c-g) photostimulated afterglow (PSAG) imaging recovered by a white LED torch (5000 lumin) for 10 s, (h) quantitatively analysis of the region of interest of the injected SCS:In,Mn AGNPs. Notably, UV light was used for pre-charging purposes prior to animal injection. After initial afterglow signals decreased overtime, the PSAG was able to be accomplished via the use of a white light LED torch. The PSAG is found to be repeated multiple times.

We then verified the low cytotoxicity of these water soluble AGNPs by in vitro cell viability MTT tests (FIG. 9). To further confirm the multiplex luminescence animal imaging concept in mice, UV-activated (254 nm) AGNPs (SCS: In, SCS:In,Tb, and SCS:In,Mn) were injected into the subcutaneous tissue of a balb/c mouse (50 μL) at three different cites, respectively. Afterglow imaging was performed by using the same set-up method in the in vitro imaging experiment (FIG. 5b). Vivid ultra-high contrast multi-channel imaging can be acquired and three logic conditions were obtained as (Y, N, N), (Y, Y, N) and (Y, Y, Y) by using the filter set. From the decision table (Table 1), one can easily tell that they are SCS:In, SCS:In,Tb, and SCS:In,Mn AGNPs, respectively. It should be noted that the quite short exposure time of 1 s during the process of imaging was sufficient because of the outstanding brightness of these multicolor afterglow particles. The signal-to-background ratios can reach 8.1×10⁵, 1.7×10⁶, 4.2×10⁶ for SCS:In, SCS:In,Tb, and SCS:In,Mn, respectively. More importantly, when the initial luminescent signals gradually attenuate along with the decay of the afterglow emission, these multicolor AGNPs can also be recharged or photostimulated in vivo and in situ by a long wavelength white LED torch (5000 lumin) for 10 s for each cycle so as to regain the afterglow property for multiple times (FIG. 10). (Wang, et al. 2016 *Inorg Chem* 55, 12822; Rodriguez et al. 2015 *Adv Opt Mater* 3, 551.)

EXPERIMENTAL

Materials

Tetraethoxysilane (TEOS), ethanol, diethanoamine (DEA), ammonium hydrate, cetyltrimethylammonium bromide (CTAB), polyvinylpyrrolidone (Mw. 40,000), Cadmium oxide (4N), Indium(III) oxide (4N), manganese(II) chloride tetrahydrate (4N), terbium(III) oxide (4N), dysprosium(III) oxide (4N) and concentrated nitric acid were all purchased from Simga-Aldrich. $Cd(NO_3)_3$ (2 M), $In(NO_3)_3$ (0.1 M), $Tb(NO_3)_3$ (0.1 M), $Dy(NO_3)_3$ (0.1 M) stock solutions were prepared by dissolving the corresponding metal oxides in diluted nitric acid (1:2) followed by air drying at 105° C. to remove the excess amount of nitric acid and re-dissolved in deionized water. $Mn^{2+}$ solutions was prepared by dissolving its chloride salt in water.

Synthesis of Mesoporous Silica Template

Mesoporous silica nanospheres (MSNs) were synthesized according to Zhang's report.[1] Briefly, 6 mL of ethanol, 0.1 g of CTAB and 50 μL of diethanoamine were dissolved into 25 mL of water and stirred under 60° C. for half an hour to prepare a transparent solution. Then, 2 mL of tetraethoxysilane was added rapidly. The reaction was finished after stirring for another 2 hour. And mesoporous silica nanospheres (about 100 nm) were collected by centrifugation and calcination at 550° C. for two hours to remove CTAB and possible organic residues.

Synthesis of SCS Nanoparticles and Doped SCS Nanoparticles

The synthesis of SCS nanoparticles was according to previous report with minor revisions.[1,2] Briefly, a precursor solution was prepared by mixing the stock solutions of $Cd^{2+}$ (2 M), $In^{3+}$ (0.1 M), $Mn^{2+}$ (0.1M), $Tb^{3+}$ (0.1 M), $Dy^{3+}$ (0.1M) according to calculated molar ratios. The final concentration of metal ions in the precursor solution was fixed to 1 M by adding ethanol. A little amount of ethanol can facilitate the absorption of the precursor solution into the mesopores of silica templates. Generally, 200 μL of the precursor solution was mixed with 100 mg mesoporous silica and dried in a vacuum oven at 80° C. for 3 hour. The samples were then put into a muffle furnace and the temperature was slowly increased to diverse temperatures (5° C./min). SCS and doped SCS nanoparticles can be synthesized after calcination for 30 min under ambient atmosphere. According to mass conservation, the molar ratio of $CdSiO_3$ vs $SiO_2$ in the SCS product is calculated to be 6.39%. The mass ratio of $CdSiO_3$ in SCS product is 20.4% (by weight). SCS nanoparticles were dispersed into saline water, which contains 0.5% (w/v) polyvinylpyrrolidone (Mw. 40,000), using an ultrasonic cell disrupter (300 W, 10 min). The concentration of SCS nanoparticles for imaging application is ~2 mg/mL.

Cell Viability Test

The MTT (3-(4,5-dimethyl-2-thiazolyl)-2,5-diphenyl-2H-tetrazolium bromide) assay was used to study the cytotoxicity of the as-synthesized AGNPs. Hela cell was used as the tested cell line. Serial dilutions of SCS:In, SCS:In,Tb, and SCS:In,Mn, from 10 mg/L to 30 mg/L, were used.

Afterglow Imaging

Aqueous dispersions of different AGNPs (SCS:In, SCS:In,Tb and SCS:In,Mn, (5 mg/mL)) in plastic centritubes was illuminated under a 6 w UV (254 nm) mercury lamp for 5 min. Thereafter, AGNPs (50 μL) were given to the back of the mice at different sites on the back along the spinal line by subcutaneous injection. The injected mouse was immediately transferred into the IVIS imaging system with a natural prone position. The exposure time for the imaging is set to 1 s.

Characterization

The morphology of the samples was inspected using a transmission electron microscopy (TEM, Techni)) with an accelerating voltage of 80 kv. The X-ray powder diffraction (XRD) was performed on diffractometer equipped with Cu Kα radiation (λ=1.5418 Å) (Panalytical X'pert PRO, Netherlands). The afterglow spectra and decay curves of the samples were tested by using powder samples (100 mg) and a fluorospectrophotometer (FluoroMax-3, HORIBA, USA). The TSL curves were detected on a customized device (1 min delay between the cessation of the UV excitation and the start of TSL test). The afterglow imaging of the nanoparticles was conducted in a Xenogen IVIS LUMINA LT imaging system.

By using a mesoporous template method, we find that monoclinic phase $CdSiO_3$ can be generated after calcination at temperatures ≥850° C., as shown in FIG. 6. Nearly all the diffraction peaks can be attributed to the characteristic peaks of monoclinic phase $CdSiO_3$ (JCPDS card no. 00-035-0810). Note that the annealing temperature at 800° C. is too low to generate monoclinic phase $CdSiO_3$. Two diffraction peaks (labeled with #) shown in the X-ray diffraction (XRD) pattern of the sample annealed at 800° C. are from the sample holder per se. The diffraction peaks of quartz $SiO_2$ (labeled with *) start to appear at temperatures higher than 850° C. The doping of $In^{3+}$ or codoping with $In^{3+}$ and $Mn^{2+}$ does not cause any observable changes on their crystalline structure according to the XRD patterns.

Via the afterglow emissions of SCS:$In_{0.02}$ synthesized at diverse temperatures, we can see that significant blue (438 nm) afterglow emission only appears when the annealing temperature is ≥850° C., as shown in FIG. 7. The afterglow intensity keeps increasing along with the increase of annealing temperatures, possibly because of the improved crystallinity. On the hand, according to our previous research, the MSN template will lose its uniform morphology when the annealing temperature goes beyond 950° C.[1] Thus, we chose 900° C. as the optimal synthesis temperature in this study.

Applicant's disclosure is described herein in preferred embodiments with reference to the Figures, in which like numbers represent the same or similar elements. Reference throughout this specification to "one embodiment," "an embodiment," or similar language means that a particular feature, structure, or characteristic described in connection with the embodiment is included in at least one embodiment of the present invention. Thus, appearances of the phrases "in one embodiment," "in an embodiment," and similar language throughout this specification may, but do not necessarily, all refer to the same embodiment.

The described features, structures, or characteristics of Applicant's disclosure may be combined in any suitable manner in one or more embodiments. In the description, herein, numerous specific details are recited to provide a thorough understanding of embodiments of the invention. One skilled in the relevant art will recognize, however, that Applicant's composition and/or method may be practiced without one or more of the specific details, or with other methods, components, materials, and so forth. In other instances, well-known structures, materials, or operations are not shown or described in detail to avoid obscuring aspects of the disclosure.

In this specification and the appended claims, the singular forms "a," "an," and "the" include plural reference, unless the context clearly dictates otherwise.

Unless defined otherwise, all technical and scientific terms used herein have the same meaning as commonly understood by one of ordinary skill in the art. Although any methods and materials similar or equivalent to those described herein can also be used in the practice or testing of the present disclosure, the preferred methods and materials are now described. Methods recited herein may be carried out in any order that is logically possible, in addition to a particular order disclosed.

INCORPORATION BY REFERENCE

References and citations to other documents, such as patents, patent applications, patent publications, journals, books, papers, web contents, have been made in this disclosure. All such documents are hereby incorporated herein by reference in their entirety for all purposes. Any material, or portion thereof, that is said to be incorporated by reference herein, but which conflicts with existing definitions, statements, or other disclosure material explicitly set forth herein is only incorporated to the extent that no conflict arises between that incorporated material and the present disclosure material. In the event of a conflict, the conflict is to be resolved in favor of the present disclosure as the preferred disclosure.

EQUIVALENTS

The representative examples are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples and the references to the scientific and patent literature included herein. The examples contain important additional information, exemplification and guidance that can be adapted to the practice of this invention in its various embodiments and equivalents thereof.

What is claimed is:

1. A nanoparticle comprising
   $CdSiO_3$ and $SiO_2$, wherein $CdSiO_3$ and $SiO_2$ together form a hybrid crystalline monoclinic lattice matrix comprising $CdSiO_3$ and $SiO_2$ molecules, and the molar ratio of $CdSiO_3$ to $SiO_2$ is in the range from 5% to 10%;
   $In^{3+}$, as a first dopant, wherein the molar ratio of In to Cd is in the range from 1% to 4%; and
   $Dy^{3+}$ as a second dopant,
   wherein
   the nanoparticle has a substantially uniform spherical morphology sized in the range of 50 nm to 100 nm, and
   upon UV excitation, exhibits an afterglow lasting 1 hour or longer.

2. The nanoparticle of claim 1, characterized by an afterglow tunable from blue to orange by adjusting the molar ratio of the first dopant to $CdSiO_3$ and/or the molar ratio of the first dopant to the second dopant.

3. A composition comprising nanoparticles of claim 1.

4. The composition of claim 3, being an aqueous solution.

5. An ink comprising nanoparticles of claim 1.

6. A diagnostic probe comprising a nanoparticle of claim 1.

* * * * *